United States Patent [19]

Philipp et al.

[11] 4,105,778
[45] Aug. 8, 1978

[54] FUSED γ-PYRONE-2-CARBOXYLIC ACID DERIVATIVES AND PROCESS THEREFOR

[75] Inventors: Adolph H. Philipp, St. Laurent; Ivo L. Jirkovsky, Montreal, both of Canada

[73] Assignee: Ayerst, McKenna & Harrison, Ltd., Montreal, Canada

[21] Appl. No.: 831,448

[22] Filed: Sep. 8, 1977

Related U.S. Application Data

[62] Division of Ser. No. 649,113, Jan. 14, 1976, Pat. No. 4,060,619.

[51] Int. Cl.² ............................................. A61K 31/38
[52] U.S. Cl. .................................. 424/275; 424/283; 260/327 TH; 260/345.2; 260/345.7 R; 260/345.8 R
[58] Field of Search .......... 260/327 TH, 345.2, 345.7, 260/345.8; 424/275, 283

[56] References Cited

U.S. PATENT DOCUMENTS

| 3,816,467 | 6/1974 | Wright | 260/345.7 R |
|---|---|---|---|
| 3,862,144 | 1/1975 | Kaminsky | 260/345.2 |

OTHER PUBLICATIONS

Dean, et al., J. Chem. Soc., Chem. Commun., 440 (1974).

Primary Examiner—Cecilia M. Jaisle
Attorney, Agent, or Firm—Arthur E. Wilfond

[57] ABSTRACT

Compounds of formula 1

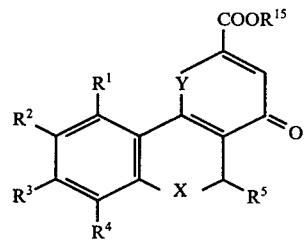

in which $R^1$, $R^2$, $R^3$ and $R^4$ are the same or different selected from the group consisting of hydrogen, halogen, nitro, trifluoromethyl, lower alkyl and lower alkoxy, or $R^1$ and $R^2$, $R^2$ and $R^3$, or $R^3$ and $R^4$ together form a $CH_2CH_2CH_2CH_2$ chain and $R^3$ and $R^4$, $R^1$ and $R^4$ and $R^1$ and $R^2$, respectively, are as defined above, $R^5$ is hydrogen, lower alkyl or a radical of formula —Alk—$OR^6$ wherein Alk is an alkylene selected from the group consisting of $CR^7R^8$, $CR^7R^8CR^9R^{10}$, $CR^7R^8CR^9R^{10}CR^{11}R^{12}$ and $CR^7R^8CR^9R^{10}CR^{11}R^{12}CR^{13}R^{14}$ wherein each of $R^7$, $R^8$, $R^9$, $R^{10}$, $R^{11}$, $R^{12}$, $R^{13}$ and $R^{14}$ is hydrogen or lower alkyl and $R^6$ is hydrogen or lower alkyl; $R^{15}$ is hydrogen or lower alkyl; X is O, S, SO or $SO_2$; Y is O or $NR^{16}$ wherein $R^{16}$ is hydrogen or lower alkyl, are disclosed. The components of formula 1 are useful for treating allergic conditions and for treating microbial infections. Methods for the preparation and use of said compounds are disclosed.

20 Claims, No Drawings

FUSED γ-PYRONE-2-CARBOXYLIC ACID DERIVATIVES AND PROCESS THEREFOR

This is a division, of application Ser. No. 649,113, filed Jan. 14, 1976 now U.S. Pat. No. 4,060,619, issued Nov. 29, 1977.

Background of the Invention (a) Field of the INVENTION

This invention relates to novel fused γ-pyrone- and γ-pyridone-2-carboxylic acid derivatives, to process for their preparation, to methods for using said derivatives, and to pharmaceutically acceptable compositions of said derivatives.

More specifically, the present invention relates to novel fused γ-pyrone- and γ-pyridone-2-carboxylic acid derivatives possessing valuable pharmacologic properties. For example, these derivatives are useful for treating allergic conditions at dosages which do not elicit undesirable side effects. Furthermore, the present derivatives exhibit useful antimicrobial properties. The combination of these pharmacologic properties together with a low order to toxicity render the fused γ-pyrone- and γ-pyridone-2-carboxylic acids of the invention therapeutically useful.

(b) Description of the Prior Art

Only a rather limited number of reports dealing with fused γ-pyrone- and γ-pyridone-2-carboxylic acids are available. One report concerns fused γ-pyrone-2-carboxylic acid derivatives of benzofuran, as described by J. B. Wright, U.S. Pat. No. 3,816,467, issued June 11, 1974. However, in this reference, the γ-pyrone-2-carobxylic acid is fused to a benzofuran whereas the γ-pyrone-2-carboxylic acids of this invention are fused to a benzopyran. Only recently fused γ-pyrone-2-methyl derivatives of benzopyran have been prepared by F. M. Dean, et al., J. Chem. Soc., Chem. Comm., 440(1974), in order to prepare the pyranopyrone nucleus of the fungal metabolite citromycetin. In addition, more recently, fused γ-pyrone-3-carboxaldehyde derivatives of dihydronaphthol have been prepared by D. Kaminsky, U.S. Pat. No. 3,862,144, issued Jan. 21, 1975. The compounds of the present invention are distinguished from the prior art compounds by having substituents at a variety of positions on the nucleus, most notably a carboxylic acid function at position 2 as well as having hetero atoms in positions 1 and 6 of the nucleus.

SUMMARY OF THE INVENTION

The fused γ-pyrone and γ-pyridone derivatives of this invention are characterized by having a crboxylic acid or ester attached to the 2-position thereof. The compounds of this invention are represented by formula 1

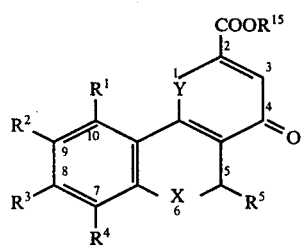

in which $R^1$, $R^2$, $R^3$ and $R^4$ are the same or different selected from the group consisting of hydrogen, halogen, nitro, trifluoromethyl, lower alkyl and lower alkoxy or $R^1$ and $R^2$, $R^2$ and $R^3$ or $R^3$ and $R^4$ together form a $CH_2CH_2CH_2CH_2$ chain and $R^3$ and $R^4$, $R^1$ and $R^4$ and $R^1$ and $R^2$, respectively, are as defined above; $R^5$ is hydrogen, lower alkyl or a radical of formula —Alk—$OR^6$ wherein Alk is an alkylene selected from the group consisting of $CR^7R^8$, $CR^7R^8CR^9R^{10}$, $CR^7R^8CR^9R^{10}CR^{11}R^{12}$ and $CR^7R^8CR^9R^{10}CR^{11}R^{12}CR^{13}R^{14}$ wherein each of $R^7$, $R^8$, $R^9$, $R^{10}$, $R^{11}$, $R^{12}$, $R^{13}$ and $R^{14}$ is hydrogen or lower alkyl and $R^6$ is hydrogen or lower alkyl; $R^{15}$ is hydrogen or lower alkyl; X is O, S, SO or $SO_2$; and Y is O or $NR^{16}$ wherein $R^{16}$ is hydrogen or lower alkyl.

A preferred group of compounds are represented by formula I

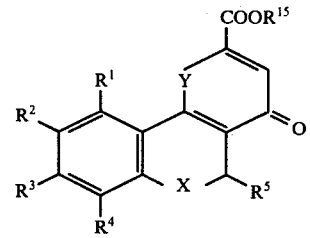

in which $R^1$, $R^2$, $R^3$ and $R^4$ are the same o different selected from the group consisting of hydrogen, halogen and lower alkyl; $R^5$ is hydrogen or lower alkyl; $R^{15}$ is hydrogen or lower alkyl; X is O, S or $SO_2$; and Y is O or $NR^{16}$ wherein $R^{16}$ is hydrogen or lower alkyl.

The compounds of formula I are prepared by a process comprising: condensing a compound of formula II

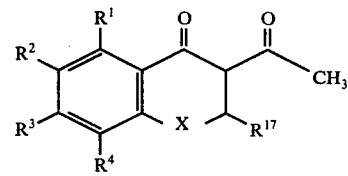

in which $R^1$, $R^2$, $R^3$, $R^4$ and X are as defined herein and $R^{17}$ is hydrogen, lower alkyl or a radical of formula —Alk—$OR^{18}$ wherein Alk is an alkylene selected from the group consisting of $CR^7R^8$, $CR^7R^8CR^9R^{10}$, $CR^7R^8CR^9R^{10}CR^{11}R^{12}$ and $CR^7R^8CR^9R^{10}CR^{11}R^{12}CR^{13}R^{14}$ wherein $R^7$, $R^8$, $R^9$, $R^{10}$, $R^{11}$, $R^{12}$, $R^{13}$ and $R^{14}$ are as defined herein and $R^{18}$ is lower alkyl or lower alkanoyl with a di(lower)alkyl oxalate of formula V

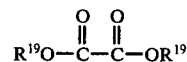

in which $R^{19}$ is lower alkyl in the presence of a strong base and reacting the product so obtained with a lower alkanol in the presence of an acid catalyst to obtain the corresponding compound of formula I in which $R^1$, $R^2$, $R^3$, $R^4$, $R^5$ and X are as defind herein, $R^{15}$ is lower alkyl and Y is O; hydrolyzing said last-named compound of formula I to obtain the corresponding compound of formula I in which $R^1$, $R^2$, $R^3$, $R^4$, $R^5$ and X are as defined herein, $R^{15}$ is hydrogen and Y is O; reacting said last-named compound of formula I with an amine of formula $R^{16}NH_2$ in which $R^{16}$ is as defined herein to obtain the corresponding compound of formula I in which $R^1$, $R^2$, $R^3$, $R^4$, $R^5$ and X are as defined herein, $R^{15}$ is hydrogen and Y is $NR^{16}$ wherein $R^{16}$ is as defined herein; and reacting said last-named compound of formula I with a lower alkanol in the presence of an acid catalyst to obtain the corresponding compound of formula I in which $R^1$, $R^2$, $R^3$, $R^4$, $R^5$ and X are as defined herein, $R^{15}$ is lower alkyl and Y is $NR^{16}$ wherein $R^{16}$ is as defined herein.

The compounds of formula I or a pharmaceutically acceptable addition salt thereof are useful for treating allergic conditions in a mammal as well as being useful for treating microbial infections in a mammal. Pharmaceutical compositions of these compounds are included as one aspect of this invention.

DETAILED DESCRIPTION OF THE INVENTION

The term "lower alkyl" as used herein contemplates both straight and branched chain alkyl radicals containing from one to six carbon atoms and includes methyl, ethyl, propyl, isopropyl, butyl, isobutyl, pentyl, hexyl and the like.

The term "lower alkoxy" as used herein contemplates both straight and branched chain alkoxy radicals containing from one to six carbon atoms and includes methoxy, ethoxy, isopropoxy, butoxy, hexanoxy and the like.

The term "lower alkanoyl" is used herein contemplates both straight and branched chain alkanoyl radicals containing from two to six carbon atoms and includes acetyl, propionyl, isobutyryl, hexanoyl and the like.

The terms "halogen" and "halo" as used herein contemplate halogens and include fluorine, chlorine, bromine, and iodine, unless stated otherwise.

The term "lower alkanol" as used herein contemplates both straight and branched chain alkanols containing from one to six carbon atoms and includes methanol, ethanol, isopropanol, butanol, hexanol and the like.

The compounds of formula I in which $R^{15}$ is hydrogen form salts with suitable pharmaceutically acceptable inorganic and organic bases. These derived salts possess the same activity as the parent acid and are included within the scope of this invention. The acid is transformed in excellent yield into the corresponding pharmaceutically acceptable salts by neutralization of said acid with the appropriate inorganic or organic base. The salts are administered in the same manner as the parent acid compounds. Suitable inorganic bases to form these salts include, for example, the hydroxides, carbonates, bicarbonates or alkoxides of the alkali metals or alkaline earth metals, for example, sodium, potassium, magnesium, calcium and the like. Suitable organic bases include the following amines; lower mono-, di- and trialkylamines, the alkyl radicals of which contain up to three carbon atoms, such as methylamine, dimethylamine, trimethylamine, ethylamine, di- and triethylamine, methylethylamine, and the like; mono-, di and trialkanolamines, the alkanol radicals of which contain up to three carbon atoms, such as mono-, di- and triethanolamine; alkylene-diamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methyl-morpholine and N-(2-hydroxyethyl)-piperidine, as well as pyridine. Furthermore, there may be mentioned the corresponding quaternary salts, such as the tetraalkyl (for example tetramethyl), alkyl-alkanol (for example methyltrimethanol and trimethyl-monoethanol) and cyclic ammonium salts, for example the N-methylpyridinium, N-methyl-N-(2-hydroxyethyl)morpholinium, N,N-dimethylmorpholinium, N-methyl-N-(2-hydroxyethyl)morpholinium, N,N-dimethylpiperidinium salts, which are characterized by having good water-solubility. In principle, there can be used all the ammonium salts which are physiologically compatible.

The transformations to the salts can be carried out by a variety of methods known in the art. For example, in the case of the inorganic salts, it is preferred to dissolve the selected acid in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the selected acid is dissolved in a suitable solvent of either moderate or low polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of low polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the selected acid with an equivalent amount of the corresponding quaternary ammonium hydroxide in water solution, followed by evaporation of the water.

Also included within the scope of this invention are the isomers of the compounds of formula I resulting from the asymmetric centers contained therein.

ANTI-ALLERGIC ACTIVITY

The compounds of this invention of formula I or a pharmaceutically acceptable salt thereof are useful in the management of allergic reactions in mammals upon oral or parenteral administration.

More specifically, the compounds of this invention are useful in the prophylatic treatment and/or management of atopic allergic manifestations, for example, bronchial asthma (e.g. hay fever), allergic rhinitis, allergic conjunctivitis, food allergies, urticaria and anaphylactoid reactions, in a sensitized mammal.

More specifically exemplified, a testing method described by I. Mota, Immunology, 7, 681 (1964) shows that the compounds of this invention block the release of mediators commonly resulting from the antigen-antibody reaction by inhibiting a positive passive cutaneous anaphylactic (PCA) test induced by the rat immunochemical counterpart of human IgE (reagin) considered indicative of such activity. In this testing method the anti-allergic activity of the compounds of formula I is demonstrated by the reduction of the wheel size of sensitized skin tissue compared to that of control animals. A comparison of the anti-allergic activity of the compounds of this invention with the anti-allergic activity of a standard compound, such as disodium cromoglycate, indicates that the compounds of this invention function in the same manner as disodium cromoglycate by blocking the release of mediators responsible for the allergic reaction. The use of the above testing method shows that therapeutic compositions containing the compounds of this invention are effective for relieving atopic allergic manifestations at dosages of 0.5 mg to 200 mg/kg body weight when administered parenterally to a mammal.

When the compounds of formula I of this invention are used for suppressing allergic manifestations of atopic immediate sensitivity in mammals, they are used alone or in combination with pharmacologically acceptable carriers, the proportion of which is determined by the solubility and the chemical nature of the compound, chosen route of administration and standard biological practice. For example, they are administered parenterally by injection; by the nasal route, for instance, as drops or aerosol, or by inhalation from an aerosol. When administering the compound of this invention as aerosols, the compound of formula I is dissolved in water or ethanol and mixed with a volatile propellant, for example, dichlorotetrafluoroethane and dichlorodifluoromethane and placed in a pressurized container having a metering valve to release a predetermined amount of material. It is preferred to use the compounds of formula I in solution in a sterile aqueous vehicle which may also contain other solutes such as buffers or preservatives, as well as sufficient quantities of pharmaceutically acceptable salts or of glucose to make the solution isotonic. In addition, the compounds of this invention can be administered in conjunction with common anti-allergics, for example, known compounds effecting anti-histaminic, analgesic, central nervous depressant, anti-hypertensive, immunosuppressive, anti-Bradykinin, anti-serotonin or endocrinological responses.

The compounds of formula I may also be administered as nasal powders or insufflations. For such purposes the compounds are administered in finely divided solid form together with a pharmaceutically acceptable solid carrier, for example, a finely divided polyethylene glycol ("Carbowax 1540") or finely divided lactose. Such compositions may also contain other excipients in finely divided solid form such as preservatives, buffers, or surface active agents.

The dosage of the compounds of this invention will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstance is reached. In general, the compounds of this invention are most desirably administered at a concentration level that will generally afford effective results without causing any harmful or deleterious side effects, and preferably at a level that is in a range of from about 0.5 mg to about 500 mg per kilogram body weight, although as aforementioned variations will occur. However, a dosage level that is in the range of from about 1.0 to about 200 mg per kilogram body weight is most desirably employed in order to achieve effective results.

ANTIBACTERIAL AND ANTIFUNGAL ACTIVITY

The compounds of this invention also exhibit utility as antibacterial agents against a number of gram-positive and gram-negative microorganisms, such as *Staphylococcus pyogenes*, both penicillin sensitive and penicillin resistant, *Streptococcus faecalis, Excherichia coli, Aerobacter aerogenes, Salmonella pullorum, Pseudomonas aeruginosa, Proteus mirabilis, Proteus vulgaris, Klebsiella pneumoniae* and *Serratia marcescens* and as antifungal agents against a number of pathogenic fungi, such as Candida albicans, *Microsporum gypseum* and *Trichophyton granulosum*, in standard tests for antibacterial and antifungal activity, such as those described in "Antiseptics, Disinfectants, Fungicides and Sterilization", G. F. Reddish, Ed., 2nd. ed., Lea and Febiger, Philadelphia, 1957 or by D. C. Grove and W. A. Randall in "Assay Methods of Antibiotics", Med. Encycl. Inc., New York 1955.

When the compounds of this invention are employed as antibacterial or antifungal agents in mammals, e.g. rats, they are administered alone or in combination with pharmacologically acceptable carriers. The proportion of the compounds is determined by the solubility and chemical nature of the compound, chosen route of administration and standard biological practice. For example, they may be administered orally in solid form containing such excipients as starch, milk sugar, certain types of clay and so forth. They may also be administered orally in the form of solutions or they may be injected parenterally. For parenteral administration they may be used in the form of a sterile solution containing other solutes, for example, enough saline or glucose to make the solution isotonic.

The dosage of the present therapeutic agents as antibiotic or antifungal agents will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford antibacterially or antifungally effective results without causing any harmful or deleterious side effects and preferably at a level that is in a range of from about 10 mg to about 1000 mg per kilo per day, although as aforementioned variations will occur. However, a dosage level that is in the range of from about 50 mg to about 500 mg per kilo per day is most desirably employed in order to achieve effective results.

In addition, the agents may be employed topically. For topical application they may be formulated in the form of solutions, creams, or lotions in pharmaceutically acceptable vehicles containing 0.1-5 percent, preferably 2 percent, by weight of the agent and may be administered topically to the infected area of the skin.

Also the antibacterial properties of the compounds of this invention may be utilized for washing equipment in hospitals, homes and farms, instruments used in medicine and bacteriology, clothing used in bacteriological laboratories, and floors, walls and ceiling in rooms in which a background free of gram-positive and gram-negative microorganisms, such as those listed above, is desired. When employed in this manner the compounds of this invention may be formulated in a number of compositions comprising the active compound and an inert material. In such compositions, while the compounds of formula I of this invention may be employed in concentrations as low as 500 p.p.m., from a practical point of view, it is desirable to use from about 0.10 percent by weight, to about 5 percent by weight or more.

The formulations that may be used to prepare antiseptic wash solutions of the compounds of this invention are varied and may readily be accomplished by standard techniques, see for example, "Remington's Practice of Pharmacy", E. W. Martin et al., Eds., 12th ed., Mack Publishing Company, Easton, Pa., 1961, pp. 1121-1150. In general, the compounds may be made up in stock solutions. They can also be formulated as suspensions in an aqueous vehicle. These make useful mixtures for decontaminating premises. Also, aqueous vehicles containing emulsifying agents, such as sodium lauryl sulfate, and relatively high concentrations, e.g. up to about 5 percent by weight, of the compounds may be formulated by conventional techniques.

PROCESSES

For the preparation of the compound of formula 1 the preferred starting material is a compound of formula II

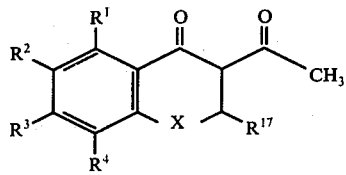

(II)

in which $R^1$, $R^2$, $R^3$, $R^4$, $R^{17}$ and X are as defined in the first instance.

The starting materials of formula II are either known, for example, 3-acetyl-6,7-dimethoxy-4-chromanone and 3-acetyl-6-methyl-4-chromanone described by Dean, et al., cited above, or they may be obtained by the following process:

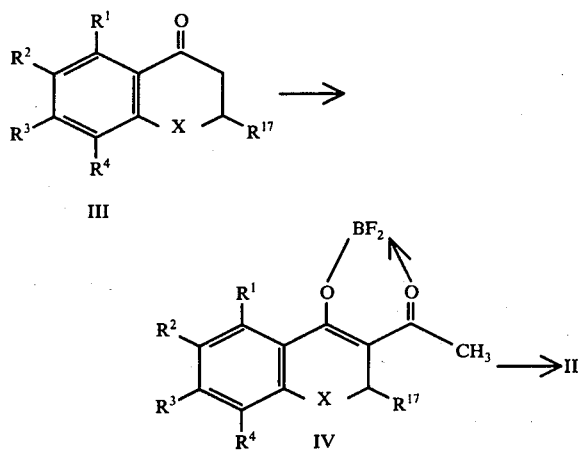

With reference to this process the compound of formula III in which $R^1$, $R^2$, $R^3$, $R^4$, $R^{17}$ and X are as defined herein is acylated preferably by treatment with boron trifluoride in the presence of acetic anhydride according to the conditions described by D. Kastner, in "Newer Methods of Preparative Organic Chemistry", Academic Press, New York, 1948, pp. 295-297 and R. M. Manyik, et al., J. Amer. Chem. Soc., 75, 5030 (1953), to form the corresponding boron complex of formula IV followed by treating the said boron complex of formula IV with sodium acetate to give the desired starting material of formula II.

The compounds of formula III are either known or may be prepared according to known methods, see for example, "Heterocyclic Compounds", R. C. Elderfield, Ed., Vol. 2, John Wiley and Sons, Inc., New York, 1951, pp. 346-354 and 534-535, I. Degani et al., Bull. Sci. Fac. Chim. ind. Bologna, 24, 75 (1966), W. N. Speckamp, et al., J. Het. Chem., II, 515 (1974).

For the preparation of the compound of this invention of formula I in which Y is O and $R^1$, $R^2$, $R^3$, $R^4$, $R^5$, $R^{15}$ and X are as defined herein, the following process is both practical and convenient:

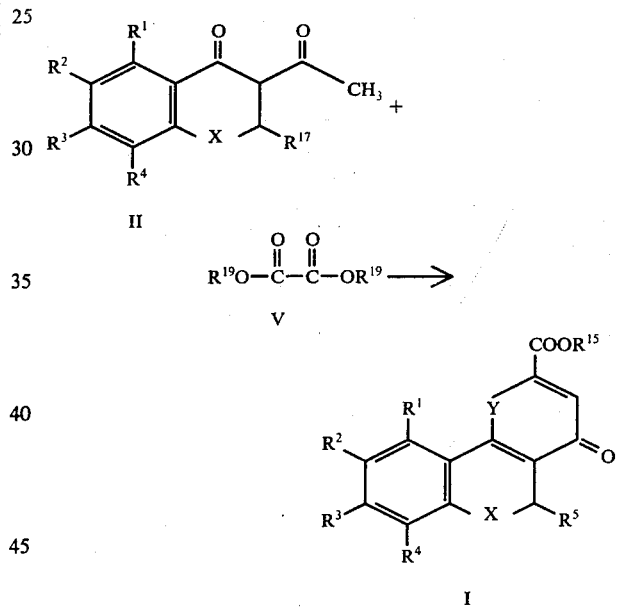

in which $R^1$, $R^2$, $R^3$, $R^4$, $R^5$, $R^{15}$, $R^{17}$ and X are as defined herein, Y is O and $R^{19}$ is lower alkyl. With reference to the above scheme the starting mateial of formula II is condensed with a di(lower)alkyl oxalate of formula V in which $R^{19}$ is lower alkyl in the presence of a strong base to obtain the corresponding compound of formula I in which Y is O and $R^{15}$ is lower alkyl and/or the corresponding compound of formula I in which Y is O and $R^{15}$ is hydrogen.

In practicing the condensation it is preferable to use a solvent as a reaction medium. Suitable inert solvents include benzene, toluene, di(lower)alkyl and cyclo(lower)alkyl ethers, for example, diethyl ether, dioxane, tetrahydrofuran, and the like. Tetrahydrofuran is especially convenient and practical for this purpose. A variety of suitable strong bases may be used for this condensation, for example, sodium amide, sodium hydride, organolithium compounds, e.g., n-butyl lithium, or an alkali metal alkoxide such as sodium methoxide, sodium ethoxide, potassium t -butoxide and the like. Sodium hydride is the preferred stong base. A convenient and practical method to practice this condensation is to add a solution containing the starting material of formula II to a slurry of the strong base, preferably three to four molar equivalents in the same solvent, and to stir the resulting mixture for about ten minutes to five hours, preferably for 30 minutes to two hours, at a temperature ranging from about −20° C to the boiling point of the reaction mixture, preferably from about 20° to 100° C. At this point a solution of a molar excess of a di(lower-)alkyl oxalate of formula V, preferably one to two molar equivalents of diethyl oxalate, preferably in the same solvent as above, is slowly added preferably under an inert atmosphere, for example, nitrogen. The reaction mixture is stirred for five to 60 hours, preferably for 10 to 30 hours. The temperature of the reaction may range from 0° C to the boiling point of the reaction mixture, however, a range from 20° to 100° C is preferred. The compound of formula I is separated from the reaction mixture by conventional methods, for instance, see examples herein.

In addition to said compound of formula I isolated from the above reaction, the corresponding triketo acid of formula VI

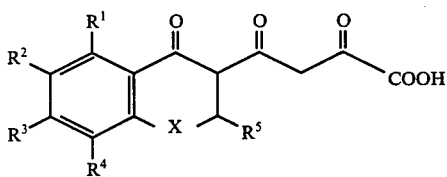

in which $R^1$, $R^2$, $R^3$, $R^4$, $R^5$ and X are as defined herein and/or the corresponding triketo ester of formula VII

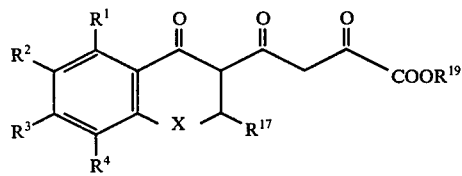

in which $R^1$, $R^2$, $R^3$, $R^4$, $R^{17}$, $R^{19}$ and X are as defined herein can be also isolated. The triketo acid of formula VI and the triketo ester formula VII are readily cyclized to give the corresponding compound of formula I. The triketo acid is conveniently cyclized by heating without solvent at about 100° to 250° C, or alternatively, heating said acid in an inert solvent, for example, in those solvents described immediately above for the condensation or in a lower alkanol, at from about 20° C to the boiling point of the reaction mixture.

A preferred method for cyclization of said triketo acid and ester comprises heating a solution of said triketo acid of formula VI and/or triketo ester of formula VII in a lower alkanol, preferably methanol or ethanol, in the presence of a suitable acid catalyst, at a temperature of from about 20° C to the boiling point of the reaction mixture for about ten hours to four days. A variety of suitable acid catalysts can be used for this cyclization, for example, hydrogen chloride, hydrogen bromide, sulfuric acid, polyphosphoric acid, acetic acid, p-toluenesulfonic acid, ethanesulfonic acid, aluminosilicates ("Molecular sieves") and the like. Hydrogen chloride, sulfuric acid, and p-toluenesulfonic acid are included among the preferred acid catalysts. In this manner the corresponding ester of the compound of formula I in which $R^1$, $R^2$, $R^3$, $R^4$, $R^5$ and X are as defined herein and $R^{15}$ is lower alkyl corresponding to the lower alkanol used as solvent is obtained. The compound of formula I in which Y is O and $R^{15}$ is hydrogen or a mixture of the latter compound of formula I and/or the compound of formula I in which $R^{15}$ is lower alkyl and/or the corresponding triketo acid of formula VI and/or the corresponding triketo ester of formula VII are also converted to the corresponding compound of formula I in which $R^{15}$ is lower alkyl by the latter process.

It will be appreciated in view of the above description that the product so obtained directly from the condensation of the starting material of formula II and the di(lower)alkyl oxalate of formula V can be treated according to the latter process, i.e., with a lower alkanol in the presence of an acid catalyst, to obtain the corresponding compound of formula I in which $R^{15}$ is lower alkyl as a substantially homogeneous product. In this manner any need to separate the mixture of products obtained from the condensation is avoided and the process for the preparation of the compounds of this invention is simplified.

The latter compound of formula I in which $R^{15}$ is lower alkyl is subjected to hydrolysis, preferably under basic conditions, for example, with an aqueous and/or lower alkanol solution of an alkali metal or alkaline-earth base (e.g. sodium hydroxide, potassium hydroxide, calcium hydroxide, sodium carbonate and the like), preferably potassium hydroxide in methanol, followed by treatment with a dilute mineral acid, such as hydrochloric acid, sulfuric acid, phosphoric acid and the like, to obtain the corresponding compound of formula I in which Y is O and $R^1$, $R^2$, $R^3$, $R^4$, $R^5$ and X are as defined herein and $R^{15}$ is hydrogen.

The γ-pyridones of this invention of formula I in which Y is $NR^{16}$ wherein $R^{16}$ is hydrogen or lower alkyl and $R^1$, $R^2$, $R^3$, $R^4$, $R^5$ and X are as defined herein and $R^{15}$ is hydrogen are prepared from the above described corresponding γ-pyrones of formula I in which Y is O and $R^1$, $R^2$, $R^3$, $R^4$, $R^5$ and X are as defined herein and $R^{15}$ is hydrogen by treating the latter compounds of formula I with ammonia or with a primary amine of formula $R^{16}NH_2$ in which $R^{16}$ is lower alkyl, respectively. A preferred method for preparing said γ-pyridones comprises treating said compound of formula I in which Y is O and $R^{15}$ is hydrogen with an aqueous solution containing a molar excess of ammonia or a molar excess of said amine at a temperature from about 20° C to about 100° C, preferably at about 50° C to 100° C, for about one-half to 30 hours, preferably for about one to ten hours, to obtain said corresponding γ-pyridone of formula I in which Y is $NR^{16}$ wherein $R^{16}$ is as described hereinabove and $R^1$, $R^2$, $R^3$, $R^4$, $R^5$ and X are as described herein and $R^{15}$ is hydrogen.

The latter acid of formula I in which $R^1$, $R^2$, $R^3$, $R^4$, $R^5$ and X are as described herein, Y is $NR^{16}$ wherein $R^{16}$ is as described herein and $R^{15}$ is hydrogen is readily esterified to obtain the corresponding ester of formula I in which $R^1$, $R^2$, $R^3$, $R^4$, $R^5$, X and Y are as defined immediately above and $R^{15}$ is lower alkyl.

Suitable esterification conditions include a variety of methods; for example, ester exchange, treatment with diazomethane, or conversion of the acid to the corresponding acid halide or mixed anhydride followed by treatment of the latter with an appropriate lower alkanol, see also L. F. Fieser and M. Fieser, "Advanced Organic Chemistry", Reinhold Publishing Corporation, New York 1961, pp. 370–381.

A preferred and convenient method of esterification comprises reacting the γ-pyridone acid of formula I with a lower alkanol in the presence of 0.05 to 0.5 molar equivalents, preferably 0.1 to 0.3 molar equivalents, of an acid catalyst, for example, hydrochloric or sulfuric acid, or any of the above mentioned acid catalysts, to obtain the corresponding ester of formula I. The temperature and time of the reaction are not critical, however, the preferred temperature may range from 20° C to the boiling point of the reaction mixture and the preferred time of reaction is from 2 to 30 hours.

The following examples illustrate further this invention.

EXAMPLE 1

β-Phenoxypropionic Acid

Phenol (203 g, 2.16 moles) is added to a solution of potassium hydroxide (112 g, 2.0 mole) in water (100 ml) at 70° C. The resulting solution is maintained at a temperature of 70° C and small portions of 3-chloropropionic acid (101 g, 0.93 mole) in water (100 ml) and potassium hydroxide (44 g, 0.81 mole) in water (50 ml) are added alternately over a period of 0.5 hour. The reaction solution is heated at reflux temperature for 10 min., cooled to room temperature and washed with ether. The aqueous phase is acidified with hydrochloric acid and extracted with ether. The combined ethereal extracts are shaken with sodium carbonate solution. The aqueous part is acidified with hydrochloric acid and extracted with ether. The combined organic extracts are dried, evaporated and crystallized from ether-petroleum ether to give the title compound, m.p. 95°–97° C [lit. m.p. 97°–98° C as reported by S. G. Powell, J. Amer. Chem. Soc., 45, 2711 (1923)].

In the same manner but replacing phenol with an equivalent amount of benzenethiol, β-(phenylthio)propionic acid, m.p. 57°–59° C, is obtained. Reported m.p. for this compound is 59° C, F. Krollpfeiffer and H. Schultze, Chem. Ber., 56, 1821 (1923).

EXAMPLE 2

β-(Phenylthio)butyric Acid

Methyl crotonate (150 g, 1.5 mole) is added over a period of 15 min. to a solution at 5° C of benzenethiol (165 g, 1.5 mole) and triethylamine (10 ml) in ether (500 ml). After standing for 12 hours at room temperature the reaction mixture is distilled to give β-(phenylthio)butyric acid methyl ester as an oil, b.p. 96°–98° C/<1 mm, $\nu_{max}^{CHCl_3}$ 1730 cm$^{-1}$.

The latter compound is dissolved in 6N hydrochloric acid (1,200 ml) and the solution is heated at reflux temperature for 17 hours. The solution is cooled and extracted with ether. The organic extract is washed with saturated sodium chloride solution, dried and evaporated to give the title compound as an oil, $\nu_{max}^{CHCl_3}$ 3000 and 1713 cm$^{-1}$.

EXAMPLE 3

4-Chromanone (111; $R^1$, $R^2$, $R^3$, $R^4$ and $R^{17}$ = H and X = O)

A mixture of β-phenoxypropionic acid (34.7 g, 0.209 mole, described in Example 1) and polyphosphoric acid (285 g) is stirred at 100° C for 15 min. The red solution is poured on crushed ice and the mixture is extracted with ether. The organic phase is washed with aqueous sodium bicarbonate solution, saturated sodium chloride solution, dried and evaporated to give the title compound as an oil, $\nu_{max}^{CHCl_3}$ 1690 cm$^{-1}$. Reported m.p. for this compound is 38° C, see S. G. Powell, cited above.

In the same manner but replacing β-phenoxypropionic acid with an equivalent amount of β-(phenylthio)propionic acid (described in Example 1) or β-(phenylthio)butyric acid (described in Example 2) and replacing polyphosphoric acid with concentrated sulfuric acid, 4-thiochromanone, $\nu_{max}^{CHCl_3}$ 1680 cm$^{-1}$ (reported m.p. for this compound is 29°–30° C, see F. Frollpfeiffer and H. Schultze, cited above) and 2-methyl-4-thiochromanone, $\nu_{max}^{CHCl_3}$ 1675 cm$^{-1}$, are obtained, respectively.

By following the procedure of Example 1 or 2 followed by the procedure of Example 3 and using the appropriately substituted phenol or benzenethiol and β-halopropionic acid or crotonate then other substituted 4-chromanones or 4-thiochromanones of formula III are obtained. More specifically exemplified, the replacement of phenol in Example 1 with an equivalent amount of p-chlorothiophenol, p-toluenethiol, p-(n-butyl)benzenethiol, p-(sec-butyl)benzenethiol, or 2-methyl-5-chlorobenzenethiol, followed by the procedure of Example 3, gives 6-chloro-4-thiochromanone, m.p. 67°–69° C, 6-methyl-4-thiochromanone, m.p. 40°–41° C, 6-(n-butyl)-4-thiochromanone, 6-(sec-butyl)-4-thiochromanone, and 5-chloro-8-methyl-4-thiochromanone, m.p, 67°–69° C, respectively.

EXAMPLE 4

3-Acetyl-4-chromanone Boron Difluoride Complex (IV; $R^1$, $R^2$, $R^3$, $R^4$ and $R^{17}$ = H, and X = O)

A solution of 4-chromanone (35.6 g, 0.24 mole, described in Example 3) in glacial acetic acid (106 ml) and acetic anhydride (71 ml) is treated in the cold (ice-water cooling) with gaseous boron trifluoride until the solution becomes deep red and precipitation occurs. The mixture is allowed to stand overnight at room temperature. The precipitated solid is collected by filtration, washed with cold glacial acetic acid, dried, and recrystallized from chloroform-hexane to give the title compound, m.p. 197°–198° C.

In the same manner but replacing 4-chromanone with an equivalent amount of 4-thiochromanone (described in Example 3) or 2-methyl-4-thiochromanone (described in Example 3), 3-acetyl-4-thiochromanone boron difluoride complex, m.p. 183°–185° C, and 3-acetyl-2-methyl-4-thiochromanone boron difluoride complex, m.p. 132°–135° C, are obtained respectively.

EXAMPLE 5

3-Acetyl-4-chromanone (II, $R^1$, $R^2$, $R^3$, $R^4$ and $R^{17}$ = H, and X = O)

A solution of 3-acetyl-4-chromanone boron difluoride complex (13 g, 54.5 mmoles, described in Example 4) and anhydrous sodium acetate (52 g) in glacial acetic acid (235 ml) is heated on a steam bath for one hr. The solution is poured on ice and the resulting mixture is extracted with ether. The organic extract is washed with aqueous sodium bicarbonate solution and saturated sodium chloride solution, dried and evaporated. The residue is subjected to chromatography on silica gel using benzene-hexane (1:1) as eluant. Evaporation of the eluate gives the title compound, m.p. 73°–74° C, $\nu_{max}^{CHCl_3}$ 1600 cm$^{-1}$.

In the same manner but replacing 3-acetyl-4-chromanone boron difluoride complex with an equivalent amount of 3-acetyl-4-thiochromanone boron difluoride complex (described in Example 4) or 3-acetyl-2-methyl-4-thiochromanone boron difluoride complex (described in Example 4), 3-acetyl-4-thiochromanone, m.p. 86°–87° C, and 3-acetyl-2-methyl-4-thiochromanone, m.p. 81°–83° C, are obtained, respectively.

By following the procedure of Examples 4 and 5 using the appropriately substituted compound of formula III then other compounds of formula II, for example, those described as starting materials in Examples 6, 7 and 9–44, are obtained. For example, the replacement of 4-chromanone in Example 4 with an equivalent amount of 6-chloro-4-thiochromanone, 6-methyl-4-thiochromanone, 6-butyl-4-thiochromanone, 6-(sec-butyl)-4-thiochromanone, 5-chloro-8-methyl-4-thiochromanone, 4-thiochromanone-1-oxide [described by A. G. Harrison et. al., Org. Mass. Spectr., 3,899 (1970)], or 4-thiochromanone-1,1-dioxide [described by F. Arndt, et. al., Chem. Ber., 58, 1612 (1925)], followed by the procedure of Example 5, gives 3-acetyl-6-chloro-4-thiochromanone, 3-acetyl-6-methyl-4-thiochromanone, 3-acetyl-6-butyl-4-thiochromanone, 3-acetyl-6-(sec-butyl)-4-thiochromanone, 3-acetyl-5-chloro-8-methyl-4-thiochromanone, 3-acetyl-4-thiochromanone-1-oxide, and 3-acetyl-4-thiochromanone-1,1-dioxide, respectively.

EXAMPLE 6

4-Oxo-4H,5H-[1]benzopyrano[4,3-b]pyran-2-carboxylic Acid Methyl ester (I; $R^1$, $R^2$, $R^3$, $R^4$ and $R^5$ = H, $R^{15}$ = $CH_3$, X and Y = O)

(a) A solution of 3-acetyl-4-chromanone (1.8 g, 9.5 mmoles, described in Example 5) in dry tetrahydrofuran (20 ml) is added dropwise to a suspension of 57% sodium hydride (1.17 g, 28.5 mmoles) in tetrahydrofuran (30 ml) and the mixture is heated at reflux temperature for 15 min. A solution of diethyl oxalate (1.39 g, 9.5 mmoles) is added dropwise under an atmosphere of nitrogen. The reaction mixture is heated at reflux temperature overnight and cooled to −40° C. A solution of 50% aqueous acetic acid (4 ml) is added and the reaction mixture evaporated. The residue is partitioned between chloroform and water, the organic phase is separated and the aqueous phase is re-extracted with chloroform. The combined chloroform extracts are dried and evaporated. The residue is subjected to chromatography on silica gel. Elution with chloroform affords 4-(4-chromanon-3-yl)-2,4-dioxobutyric acid ethyl ester (VII; $R^1$, $R^2$, $R^3$ $R^4$ and $R^{17}$ = H, $R^{19}$ = $C_2H_5$ and X = O), which is crystallized from ether, m.p. 117°–119° C.

(b) Solid 3-acetyl-4-chromanone (0.570 g, 3 mmoles, described in Example 5) is added in portions at room temperature to a suspension of 57% sodium hydride (0.379 g, 9 mmoles) in dry tetrahydrofuran (10 ml). The mixture is heated within 15 min to 60° C and diethyl oxalate (0.438 g, 3 mmoles) in tetrahydrofuran (10 ml) is added. After heating at reflux temperature under an atmosphere of nitrogen for 17 hr., the solvent is removed under reduced pressure, the residue is dissolved in ice-water and extracted with ether. The aqueous phase is acidified with 6N hydrochloric acid and extracted with chloroform. The organic phase is dried, evaporated, and the residue crystallized from methanol-chloroform to give 4-(4-chromanone-3-yl)-2,4-dioxobutyric acid (VI; $R^1$, $R^2$, $R^3$, $RI^4$ and $R^5$ = H, and X = O), $v_{max}^{nujol}$ 1705, 1615 and 1560 cm$^{-1}$.

(c) A solution of 4-(4-chromanone-3-yl)-2,4-dioxobutyric acid ethyl ester [0.70 g, 2.4 mmoles, described above in (a)] in methanol is saturated with hydrogen chloride gas. The solution is heated at reflux temperature overnight and evaporated to dryness. The residue is chromatographed on silica gel using benzene-ethyl acetate (4:1). The eluate is evaporated and the residue is crystallized from chlorofrom-ether to give the title compound, m.p. 173°–174° C.

(d) In the same manner as described above in (c) but replacing 4-(4-chromanone-3-yl)-2,4-dioxobutyric acid ethyl ester with an equivalent amount of the corresponding acid, 4-(4-chromanone-3-yl)-2,4-dioxobutyric acid [described above in (b)], the title compound is obtained.

In the same manner but replacing sodium hydride with an equivalent amount of sodium amide, sodium methoxide, sodium ethoxide, potassium t-butoxide or n-butyl lithium, the title compound is obtained.

EXAMPLE 7

5-Methyl-4-oxo-4H,5H-[1]benzothiopyrano[4,3-b]pyran-2-carboxylic Acid Methyl Ester (I; $R^1$, $R^2$, $R^3$ and $R^4$ = H, $R^5$ = $CH_3$, $R^{15}$ = $CH_3$, X = S and Y = O A solution of 3-acetyl-2-methyl-4-thiochromanone (17.23 g, 0.080 mole, described in Example 5) in tetrahydrofuran (60 ml) is added dropwise under an atmosphere of nitrogen to a suspension of 57% sodium hydride in mineral oil (10.1 g, 0.24 mole) in dry tetrahydrofuran (50 ml). After stirring for one hr. at room temperature the mixture is heated to 60° C and a solution of diethyl oxalate (11.69 g, 0.080 mole) in tetrahydrofuran (50 ml) is added dropwise. The mixture is heated at reflux temperature overnight and evaporated under reduced pressure. An ice-water mixture is added to the residue, the mixture is allowed to stand at room temperature for several hours and extracted with ether. The aqueous phase is acidified with hydrochloric acid and extracted with chloroform. The organic phase is dried and evaporated. The residue is dissolved in methanol (600 ml) and the solution is saturated with hydrogen chloride gas. The solution is heated at reflux temperature overnight, filtered and the filtrate is evaporated. The residue is subjected to chromatography on silica gel. Elution with chloroform and crystallization from methanol yields the title compound; m.p. 153°–155° C, $v_{max}^{CHCl_3}$ 1750 and 1650 cm$^{-1}$.

In the same manner but replacing sodium hydride with an equivalent amount of sodium amide, sodium methoxide, sodium ethoxide, potassium t-butoxide or n-butyllithium, the title compound is obtained.

In the same manner but replacing 3-acetyl-2-methyl-4-thiochromanone with an equivalent amount of other compounds of formula II and replacing methanol with other lower alkanols other γ-pyrones of formula I in which Y is O and $R^{15}$ is lower alkyl are obtained. Examples of such compounds of formula I are listed as products in Tables I and II together with the appropriate staring material of formula II used for the preparation of the γ-pyrone.

TABLE 1

Product: [(prefix listed below)-4-oxo-4H,5H-[1]benzothiopyrano[4,3-b]pyran-2-carboxylic acid (suffix listed below)]

| EX. | R¹ | R² | R³ | R⁴ | R¹⁷ | X | PREFIX//SUFFIX |
|---|---|---|---|---|---|---|---|
| 8 | H | Cl | H | H | H | S | 9-chloro //methyl ester, m.p. 220–222° C |
| 9 | H | CH₃ | H | H | H | S | 9-methyl //methyl ester, m.p. 167–168° C |
| 10 | H | n-C₄H₉ | H | H | H | S | 9-butyl //methyl ester, m.p. 134–136° C |
| 11 | Cl | H | H | CH₃ | H | S | 10-chloro-7-methyl //methyl ester, m.p. 192-194° C |
| 12 | CH₃ | H | CH₃ | H | CH₂OC₂H₅ | S | 8,10-dimethyl-5-ethoxymethyl // ethyl ester |
| 13 | Br | C₂H₅ | H | H | H | S | 10-bromo-9-ethyl //ethyl ester |
| 14 | t-C₄H₉ | H | H | H | C₆H₁₃ | S | 10(t-butyl)-5-hexyl //methyl ester |
| 15 | H | H | C₅H₁₁ | CH₃ | C₂H₄O—$\overset{O}{\overset{\|}{C}}$CH₃ | S | 5-(2-ethanol)-7-methyl-8-pentyl // methyl ester |
| 16 | C₃H₇O | H | t-C₄H₉ | H | CH₃ | S | 8-(t-butyl)-5-methyl-10propoxy // methyl ester |
| 17 | H | CH₂C(CH₃)₃ | H | NO₂ | H | S | 9-(2,2-dimethylpropyl)-7-nitro // ethyl ester |
| 18 | (CH₂)₂C(CH₃)₃ | H | H | H | C₂H₅ | S | 10-(3,3-dimethylbutyl)-5-ethyl // methyl ester |
| 19 | H | CH₃O | H | i-C₃H₇ | H | S | 7-isopropyl-9-methoxy // propyl ester |
| 20 | H | H | H | sec-C₄H₉ | CH₂OCCH₃ (O=) | S | 5-methanol-7-(1-methylpropyl) // propyl ester |
| 21 | CH₃O | H | NO₂ | H | i-C₃H₇ | S | 5-isopropyl-10-methoxy-8-nitro // propyl ester |
| 22 | H | CH₃O | H | C₄H₉O | H | S | 7-butoxy-9-methoxy // methyl ester |
| 23 | H | CH₃ | CH₃ | CH₃ | H | S | 7,8,9-trimethyl // methyl ester |
| 24 | Cl | H | (CH₂)₂C(CH₃)₃ | H | C₂H₅ | S | 10-chloro-8-(3,3-dimethylbutyl)-5-ethyl // ethyl ester |
| 25 | H | sec-C₄H₉ | H | H | H | S | 9-(1-methylpropyl) //methyl ester |
| 26 | H | H | H | H | H | SO | no prefix //-6-oxide methyl ester |
| 27 | CH₃ | H | Cl | H | H | SO | 8-chloro-10-methyl//-6-oxide ethyl ester |
| 28 | H | n-C₄H₉ | H | H | (CH₂)₃OCH₃ | SO | 9-butyl-5-(3-methoxypropyl) //-6-oxide ethyl ester |
| 29 | H | H | H | C₂H₅ | CH₃ | SO | 7-ethyl-5-methyl //-6-oxide methyl ester |
| 30 | H | H | H | H | H | SO₂ | no prefix //-6,6-dioxide, methyl ester mp 212-214° C |
| 31 | Br | CH₃ | H | H | H | SO₂ | 10-bromo-9-methyl //-6,6-dioxide ethyl ester |
| 32 | H | H | i-C₃H₇ | H | (CH₂)₄OCCH₃ (O=) | SO₂ | 5-(4-butanol)-8-isopropyl // -6,6-dioxide propyl ester |
| 33 | C₅H₁₁ | H | H | I | H | SO₂ | 7-iodo-10-pentyl //-6,6-dioxide propyl ester |
| 34 | H | NO₂ | H | C₃H₇O | CH₂CH(CH₃)—OC₂H₅ | SO₂ | 5-[2-ethoxy-2-methyl)ethyl]-9-nitro-7-propoxy //-6,6-dioxide methyl ester |

TABLE II

Product: [(prefix listed below)-4-oxo-4H,5H-[1]benzopyrano[4,3-b]pyran-2-carboxylic acid (suffix listed below)]

| EX. | R¹ | R² | R³ | R⁴ | R¹⁷ | X | PREFIX//SUFFIX |
|---|---|---|---|---|---|---|---|
| 35 | C₂H₅ | H | H | NO₂ | H | O | 10-ethyl-7-nitro // methyl ester |
| 36 | H | i-C₃H₇ | H | H | C₂H₅ | O | 5-ethyl-9-isopropyl//propyl ester |
| 37 | H | H | I | C₂H₅O | C₄H₈OCCH₃ (O=) | O | 5-(4-butanol)-7-ethoxy-8-iodo//ethyl ester |
| 38 | H | NO₂ | Cl | H | C₃H₇ | O | 8-chloro-9-nitro-5-propyl//propyl ester |
| 39 | NO₂ | Br | H | H | C₂H₄OC₃H₇ | O | 9-bromo-10-nitro-5-(2-propoxyethyl) // ethyl ester |
| 40 | Br | H | F | H | H | O | 10-bromo-8-fluoro // propyl ester |
| 41 | I | H | C₂H₅O | H | C₄H₇(C₂H₅)OCH₃ | O | 8-ethoxy-10-iodo-5-[(4-ethyl-4-methoxy)butyl]//butyl ester |
| 42 | H | sec-C₄H₉ | C₂H₅ | H | C₃H₆OCCH₃ (O=) | O | 8-ethyl-9-(1-methylpropyl)-5-(3-propanol) //methyl ester |

EXAMPLE 43

4-Oxo-4H,5[1]1]benzopyrano[4,3-b]pyran-2-carboxylic Acid (T; R¹, R², R³, R⁴, R⁵ and R¹⁵ = H, X and Y = O)

A solution of 4-oxo-4H,5H-[1]benzopyrano[4,3-b]pyran-2-carboxylic acid methyl ester (0.292 g, 1.1 moles, described in Example 6) in methanol (15 ml) containing potassium hydroxide (0.2 g) is stirred at room temperature overnight. The solution is evaporated under reduced pressure and the residue is crystallized from methanol to give 4-oxo-4H,5H-[1]benzopyrano[4,3-b]pyran-2-carboxylic acid potassium salt; m.p. > 280° C, $v_{max}^{nujol}$ 1650 cm⁻¹. The latter compound is dissolved in water and the resulting solution is added to dilute hydrochloric acid. The precipitate is collected and crystallized from methanol to give the title compound; m.p. 253°–254° C (dec.), $v_{max}^{nujol}$ 2500, 1735 and 1650 cm⁻¹.

In the same manner but replacing 4-oxo-4H,5H-[1]benzopyrano[4,3-b]pyran-2-carboxylic acid methyl ester with an equivalent amount of 5-methyl-4-oxo-4H, 5H-[1]benzothiopyrano[4,3-b]pyran-2-carboxylic acid methyl ester (described in Example 7), 5-methyl-4-oxo-4H,5H-[1]benzothiopyrano[4,3-b]pyran-2-carboxylic acid (I; $R^1$, $R^2$, $R^3$, $R^4$ and $R^{15}$ = H, $R^5$ = $CH_3$, X = S and Y = O) m.p. 215°–217° C (dec.) is obtained. The latter compound (2.0 g, 7.3 moles) is added to a methanolic solution of 2-aminoethanol (0.445 g, 7.3 mmoles) and methanol is added until a clear solution is obtained. The solution is concentrated under reduced pressure and ether is added to induce crystallization of 5-methyl-4-oxo-4H,5H-[1]benzothopyrano[4,3-b]-pyran-2-carboxylic acid 2-aminoethanol salt, m.p. 163°–165° C.

By following the procedure of Example 43 using the appropriate γ-pyrone ester of formula I in which $R^{15}$ is lower alkyl, other γ-pyrones of formula I in which $R^{15}$ is hydrogen are obtained. Examples of the latter γ-pyrones are listed as products in Tables III and IV together with the appropriate starting γ-pyrone ester. In each case the starting material is noted by the number of the example in which it is prepared.

TABLE III

| Ex. | NO. of the Example in which is prepared | Product: [(prefix listed below)-4-oxo-4H,5H-[1]benzothiopyrano[4,3-b]pyran-2-carboxylic acid (suffix listed below)] PREFIX//SUFFIX |
|---|---|---|
| 44 | 8 | 9-chloro //no suffix, m.p. 283° C(dec); potassium salt, m.p. >280° C; 2-aminoethanol salt, m.p. 215-217° C (dec) |
| 45 | 9 | 9-methyl //no suffix, m.p. 282–283° C (dec.); 2-aminoethanol salt, m.p. 217-219° C (dec.) |
| 46 | 10 | 9-butyl //no suffix, m.p. 228-14 230° C (dec.); 2-aminoethanol salt, m.p. 197–199° C (dec.) |
| 47 | 11 | 10-chloro-7-methyl //no suffix, m.p. 264-267° C (dec.); 2-aminoethanol salt, m.p. 107-110° C (softening) |
| 48 | 12 | 8,10-dimethyl-5-ethoxymethyl//no suffix |
| 49 | 13 | 10-bromo-9-ethyl //no suffix |
| 50 | 14 | 10(t-butyl)-5-hexyl //no suffix |
| 51 | 15 | 5-(2-ethanol)-7-methyl-8-pentyl //no suffix |
| 52 | 16 | 8-(t-butyl)-5-methyl-10-propoxy //no suffix |
| 53 | 17 | 9-(2,2-dimethylpropyl)-7-nitro //no suffix |
| 54 | 18 | 10-(3,3-dimethylbutyl)-5-ethyl //no suffix |
| 55 | 19 | 7-isopropyl-9-methoxy //no suffix |
| 56 | 20 | 5-methanol-7-(1-methylpropyl)// no suffix |
| 57 | 21 | 5-isopropyl-10-methoxy-8-nitro // no suffix |
| 58 | 22 | 7-butoxy-9-methoxy //no suffix |
| 59 | 23 | 7,8,9-trimethyl //no suffix |
| 60 | 24 | 10-chloro-8-(3,3-dimethylbutyl)-5-ethyl //no suffix |
| 61 | 25 | 9-(1-methylpropyl) //no suffix mp 261–262° C (dec.) |
| 62 | 26 | no prefix //-6-oxide |
| 63 | 27 | 8-chloro-10-methyl //-6-oxide |
| 64 | 28 | 9-butyl-5-(3-methoxypropyl)//-6-oxide |
| 65 | 29 | 7-ethyl-5-methyl //-6-oxide |
| 66 | 30 | no prefix //-6,6-dioxide, mp 272–274° C (dec.) |
| 67 | 31 | 10-bromo-9-methyl //-6,6-dioxide |
| 68 | 32 | 5-(4-butanol)-8-isopropyl // -6,6,-dioxide |
| 69 | 33 | 7-iodo-10-pentyl //-6,6,-dioxide |
| 70 | 34 | 5-[(2-ethoxy-2-methyl)ethyl]-9-nitro-7-propoxy //-6,6-dioxide |

TABLE IV

| Ex. | No. of the example in which starting material is prepared | Product: [(prefix listed below)-4-oxo-4H,5H-[1]benzopyrano[4,3-b]pyran-2-carboxylic acid] PREFIX |
|---|---|---|
| 71 | 35 | 10-ethyl-7-nitro |
| 72 | 36 | 5-ethyl-9-isopropyl |
| 73 | 37 | 5-(4-butanol)-7-ethoxy-8-iodo |
| 74 | 38 | 8-chloro-9-nitro-5-propyl |
| 75 | 39 | 9-bromo-10-nitro-5-(2-propoxyethyl) |
| 76 | 40 | 10-bromo-8-fluoro |
| 77 | 41 | 8-ethoxy-10-iodo-5-[(4-ethyl-4-methoxy)butyl] |
| 78 | 42 | 8-ethyl-9-(1-methylpropyl)-5-(3-propanol) |

EXAMPLE 79

4-Oxo-4H,5H-[1]benzothiopyrano[4,3-b]pyran-2-carboxylic Acid (I; $R^1$, $R^2$, $R^3$, $R^4$, $R^5$ and $R^{15}$ = H, X = S and Y = O)

A solution of 3-acetyl-4-thiochromanone (6.18 g, 0.03 mole, described in Example 5) and diethyl oxalate (4.38 g, 0.03 mole) in tetrahydrofuran (25 ml) is added dropwise to a stirred suspension of 57% sodium hydride (3.79 g, 0.09 mole) in tetrahydrofuran (25ml) under an atmosphere of nitrogen at 70°. After the addition is completed, the mixture is heated under an atmosphere of nitrogen at 70° C for 17 hr and the solvent removed by evaporation under reduced pressure. The residue is dissolved in water and washed with ether. The aqueous phase is acidified with concentrated hydrochloric acid (15 ml) in the presence of chloroform and the mixture is stirred for 1.5 hr. at room temperature. The organic phase is separated and the aqueous phase is extracted with chloroform. The combined organic extracts are dried, evaporated and the resulting residue crystallized from chloroform to give the title compound; m.p. 251°–253° C, $v_{max}^{nujol}$ 2500, 1890, 1730, 1640, 1575, 1550 and 1265 cm$^{-1}$.

In the same manner but replacing sodium hydride with an equivalent amount of sodium amide, sodium methoxide, sodium ethoxide, potassium ±-butoxide or n-butyl lithium, the title compound is obtained.

The corresponding 2-aminoethanol salt of the title compound is prepared by adding a solution of 2-aminoethanol (0.962 g, 15.77 mmoles) in methanol (5 ml) to a suspension of the title compound (4.1 g, 15.77 mmoles) in methanol (50ml). The resulting clear solution is concentrated under reduced pressure and an excess of hot acetonitrile is added. Cooling produces crystals of the 2-aminoethanol salt of the title compound, m.p. 170°–172° C.

In the same manner but replacing 3-acetyl-4-thiochromanone with an equivalent amount of 2-acetyl-1-oxo-2,3,7,8,9,10-hexahydro-1H-naphtho[2,1-b]thipyran, 3-acetyl-4-oxo-2,3,6,7,8,9-hexahydro-4H-naphtho[2,3-b]thiopyran, 3-acetyl-4-oxo-2,3,7,8,9,10-hexahydro-4H-naphtho[1,2-b]thiopyran, 2-acetyl-1-oxo-2,3,7,8,9,10-hexahydro-1H-naphtho[2,1-b]pyran, 3-acetyl-4-oxo-2,3,6,7,8,9-hexahydro-4H-naphtho[2,3-b]pyran, 3-acetyl-4-oxo-2,3,7,8,9,10-hexahydro-4H-naphtho[1,2-b]pyran, 3-acetyl-4-oxo-2,3,6,7,8,9-hexahydro-4H-naphtho[2,3-b]thiopyran-1,1-dioxide, or 2-acetyl-3-methoxymethyl-1-oxo-2,3,7,8,9,10-hexahydro-1H-naphtho[2,1-b]thiopyran-4,4-dioxide, the following acids are obtained respectively:
4-oxo-9,10,11,12-tetrahydro-4H,5H-naphtho[2,1-b]thiopyrano[2,3-d]pyran-2-carboxylic acid (I; $R^3$, $R^4$, $R^5$ and $R^{15}$ = H, $R^1$ and $R^2$ together form a $CH_2CH_2CH_2CH_2$ chain, X = S and Y = O), 4-oxo-8,9,10,11-tetrahydro-4H,5H-naphtho[2,3-b]thiopyrano[2,3-b]pyran-2-carboxylic acid (I; $R^1$, $R^4$, $R^5$ and $R^{15}$ = H, $R^2$ and $R^3$ together form a $CH_2CH_2CH_2CH_2$ chain, X = S and Y = O), 4-oxo-7,8,9,10-tetrahydro-4H,5H-naphtho[1,2-b]thiopyrano[2,3-d] pyran-2-carboxylic acid (I; $R^1$, $R^2$, $R^5$ and $R^{15}$ = H, $R^3$ and $R^4$ together form a $CH_2CH_2CH_2CH_2$ chain, X = S and Y = O), 4-oxo-9,10,11,12-tetrahydro-4H,5H-naphtho[2,1-b]pyrano[2,3-d]pyran-2-carboxylic acid (I; $R^3$, $R^4$, $R^5$ and $R^{15}$ = H, $R^1$ and $R^2$ together form a $CH_2CH_2CH_2CH_2$ chain and X = Y = O), 4-oxo-8,9,10,11-tetrahydro-4H,5H-naphtho[2,3-b]pyrano[2,3-d]pyran-2-carboxylic acid (I; $R^1$, $R^4$, $R^5$ and $R^{15}$ = H, $R^2$ and $R^3$ together form a $CH_2CH_2CH_2CH_2$ chain and X = Y = O), 4-oxo-7,8,9,10-tetrahydro-4H,5H-naphtho[1,2-b]pyrano[2,3-d]pyran-2-carboxylic acid (I; $R^1$, $R^2$, $R^5$ and $R^{15}$ = H, $R^3$ and $R^4$ together form a $CH_2CH_2CH_2CH_2$ chain and X = Y = O, 4-oxo-8,9,10,11-tetrahydro-4H,5H-naphtho[2,3-b]thiopyrano[2,3-d]pyran-2-carboxylic acid-6,6-dioxide (I; $R^1$, $R^4$, $R^5$ and $R^{15}$ = H, $R^2$ and $R^3$ together form a $CH_2CH_2CH_2CH_2$ chain, X = $SO_2$ and Y = O) and 3-methoxymethyl-4-oxo-9,10,11,12-tetrahydro-4H,5H-naphtho[2,1-b]thiopyrano[2,3-d]pyran-2-carboxylic acid-6,6-dioxide (I; $R^3$, $R^4$ and $R^{15}$ = H; $R^1$ and $R^2$ together form a $CH_2CH_2CH_2CH_2$ chain, $R^5$ = $CH_2OCH_3$, X = $SO_2$ and Y = O).

EXAMPLE 80

1,4-Dihydro-4-oxo-5H-[1]benzothiopyrano[4,3-b]pyridine-2-carboxylic Acid (I; $R^1$, $R^2$, $R^3$, $R^4$, $R^5$ and $R^{15}$ = H, X = S and Y = NH)

A solution of 4-oxo-4H,5H-[1]benzothiopyrano[4,3-b]pyran-2-carboxylic acid (3.0 g, 11.53 mmoles, described in Example 79) in concentrated ammonium hydroxide (50 ml) is heated on a steam bath for 2.5 hr., and evaporated under reduced pressure. The residue is dissolved in water (75 ml) and added to a mixture of concentrated hyrochloric acid (5 ml) and ice. The precipitate is collected, washed with 0.07 N hydrochloric acid, acetone and ether to give the title compound as light yellow crystals, m.p. 256°-257° C.

The title compound (2.49 g, 9.61 mmoles) is dissolved in a methanolic solution of 2-aminoethanol (0.596 g, 9.77 mmoles). The resulting brown solution is treated with charcoal, filtered and the filtrate is evaporated. Crystallization of the residue from methanolether gives the 2-aminoethanol salt of the title compound, m.p. 158°-161° C.

In the same manner but replacing the concentrated ammonium hydroxide with an equivalent amount of methylamine (40% aqueous solution), ethylamine (40% aqueous solution), isopropylamine (40% aqueous solution) and hexylamine (40% aqueous solution), 1-methyl-1,4-dihydro-4-oxo-5H-[1]benzothiopyrano[4,3-b]-pyridine-2-carboxylic acid, m.p. 203°-204° C, 2-aminoethanol salt, m.p. 120°-160° C, 1-ethyl-1,4-dihydro-4-oxo-5H-[1]benzothiopyrano[4,3-b]-pyridine-2-carboxylic acid, 1-isopropyl-1,4-dihydro-4-oxo-5H-[1]-benzothiopyrano[4,3-b]pyridine-2-carboxylic acid and 1-hexyl-1,4-dihydro-4-oxo-5H-[1]benzothiopyrano[4,3-b]pyridine-2-carboxylic acid are obtained, respectively.

In the same manner, by using an appropriate amine of formula $R^{16}NH_2$ but replacing 4-oxo-4H,5H-[1]benzothiopyrano[4,3-b]pyran-2-carboxylic acid with an equivalent amount of one of the 4-oxo-tetrahydro-4H,5H-naphtho[2,1-b] or [2,3-b] or [1,2-b]thiopyrano[2,3-d]pyran-2-carboxylic acids (described in Example 79), 4-oxo-1,4,9,10,11,12-hexahydro-5H-naphtho[1',2' : 5,6]thiopyrano[4,3-b]pyridine-2-carboxylic acid (I; $R^3$, $R^4$, $R^5$ and $R^{15}$ = H, $R^1$ and $R^2$ together form a $CH_2CH_2CH_2CH_2$ chain, X = S and Y = NH), 4-oxo-1,4,8,9,10,11-hexahydro-5H-naphtho[2', 3' : 5,6]thiopyrano]4,3-b]pyridine-2-carboxylic acid (I; $R^1$, $R^4$, $R^5$ and $R^{15}$ = $R^2$ and $R^3$ together form a $CH_2CH_2CH_2CH_2$ chain, X = S and Y = NH), 4-oxo-1,4,7,8,9,10-hexahydro-5H-naphtho[2',1' : 5,6]thiopyrano[4,3-b]pyridine-2-carboxylic acid (I; $R^1$, $R^2$, $R^5$ and $R^{15}$ = H, $R^3$ and $R^4$ together form a $CH_2CH_2CH_2CH_2$ chain, X = S and Y = NH), 1-ethyl-4-oxo-1,4,8,9,10,11-hexahydro-5H-naphtho[2', 3' : 5,6]thiopyrano[4,3-b]pyridine-2-carboxylic acid-6,6-dioxide (I; $R^1$, $R^4$, $R^5$ and $R^{15}$ = H, $R^2$ and $R^3$ together form a $CH_2CH_2CH_2CH_2$ chain, X = $SO_2$ and Y = $NC_2H_5$) and 3-methoxymethyl-4-oxo-1,4,9,10,11,12-hexahydro-5H-naphtho[1', 2' : 5,6]thiopyrano[4,3-b]pyridine-2-carboxylic acid-6,6-dioxide (I; $R^3$, $R^4$ and $R^{15}$ = H, $R^1$ and $R^2$ together form a $CH_2CH_2CH_2CH_2$ chain, $R^5$ = $CH_2OCH_3$, X = $SO_2$ and Y = NH) are obtained, respectively.

By following the procedure of Example 80 using the appropriate γ-pyrone of formula I, other γ-pyridones of formula I in which Y is $NR^{16}$ are obtained. Examples of such γ-pyridones of formula I are listed as products in Tables V and VI together with the appropriate starting γ-pyrone of formula I and the aqueous amine of formula $R^{16}NH_2$ used for the preparation of the γ-pyridone. In each case the starting material is noted by the number of the example in which it is prepared.

TABLE V

| Example | No.of the Example in which starting material is prepared | Amine of formula $NH_2$—$R^{16}$ | Product: [(prefix listed below)-1,4-dihydro-4-oxo-5H-[1]benzothiopyrano-[4,3-b]pyridine-2-carboxylic acid [suffix listed below)] Prefix//Suffix |
|---|---|---|---|
| 81 | 43 | $NH_3$ | 5-methyl//no suffix |
| 82 | 44 | $NH_3$ | 9-chloro//no suffix, m.p. 282–283° C (dec.);2-aminoethanol salt, m.p. 242–243° C (dec.) |
| 83 | 45 | $NH_3$ | 9-methyl//no suffix, m.p. 280–281° C (dec.); 2-aminoethanol salt, m.p. 22714 230° C (dec.) |
| 84 | 46 | $NH_3$ | 9-butyl//no suffix, m.p. 273–274° C (dec.); 2-aminoethanol salt, m.p. 204–206° C (dec.) |
| 85 | 47 | $NH_3$ | 10-chloro-7-methyl//no suffix, m.p. 272–273° C (dec.); 2-aminoethanol salt, m.p. 202–204° C (dec. |

TABLE V-continued

| Example | No.of the Example in which starting material is prepared | Amine of formula $NH_2$—$R^{16}$ | Product: [(prefix listed below)-1,4-dihydro-4-oxo-5H-[1]benzothiopyrano-[4,3-b]pyridine-2-carboxylic acid [suffix listed below)] Prefix//Suffix |
|---|---|---|---|
| 86 | 48 | $NH_3$ | 8,10-dimethyl-5-ethoxymethyl//no suffix |
| 87 | 49 | $C_2H_5NH_2$ | 10-bromo-1,9-diethyl//no suffix |
| 88 | 50 | $C_4H_9NH_2$ | 1-butyl-10-(t-butyl)-5-hexyl//no suffix |
| 89 | 51 | sec-$C_4H_9NH_2$ | 5-(2-ethanol)-7-methyl-1-(1-methylpropyl)-8-pentyl//no suffix |
| 90 | 52 | $CH_3NH_2$ | 8-(t-butyl)-1,5-dimethyl-10-propoxy//no suffix |
| 91 | 53 | $C_6H_{13}NH_2$ | 9-(2,2-dimethylpropyl)-1-hexyl-7-nitro//no suffix |
| 92 | 54 | $C_3H_7NH_2$ | 10-(3,3-dimethylbutyl)-5-ethyl-1-propyl//no suffix |
| 93 | 55 | $C_2H_5NH_2$ | 1-ethyl-7-isopropyl-9-methoxy//no suffix |
| 94 | 56 | $NH_3$ | 5-methanol-7-(1-methylpropyl)//no suffix |
| 95 | 57 | $CH_3NH_2$ | 5-isopropyl-10-methoxy-1-methyl-8-nitro//no suffix |
| 96 | 58 | $C_5H_{11}NH_2$ | 7-butoxy-9-methoxy-1-pentyl//no suffix |
| 97 | 59 | $CH_3NH_2$ | 1,7,8,9-tetramethyl//no suffix |
| 98 | 60 | $NH_3$ | 10-chloro-8-(3,3-dimethylbutyl)-5-ethyl//no suffix |
| 99 | 61 | $NH_3$ | 9-(1-methylpropyl)//no suffix, m.p. 269° C (dec.) |
| 100 | 62 | $C_2H_5NH_2$ | 1-ethyl//-6-oxide |
| 101 | 63 | $OC_3H_7NH_2$ | 8-chloro-10-methyl-1-propyl//-6-oxide |
| 102 | 64 | $NH_3$ | 9-butyl-5-(3-methoxypropyl)//-6-oxide |
| 103 | 65 | $CH_3NH_2$ | 7-ethyl-1,5-dimethyl//-6-oxide |
| 104 | 66 | $NH_3$ | no prefix//-6,6-dioxide |
| 105 | 67 | $C_2H_5NH_2$ | 10-bromo-1-ethyl-9-methyl//-6,6-dioxide |
| 106 | 68 | $C_4H_9$—$NH_2$ | 5-(4-butanol)-1-butyl-8-isopropyl//-6,6-dioxide |
| 107 | 69 | $CH_3NH_2$ | 7-iodo-1-methyl-10-pentyl//-6,6-dioxide |
| 108 | 70 | $NH_3$ | 5-[(2-ethoxy-2-methyl)ethyl]-9-nitro-7-propoxy//-6,6-dioxide |

TABLE VI

| Example | No. of the Example in which starting material is prepared | Amine of formula $NH_2$—$R^{16}$ | Product: [(prefix listed below)-1,4-dihydro-4-oxo-5H-[1]benzopyrano[4,3-b]-pyridine-2-carboxylic acid] Prefix |
|---|---|---|---|
| 109 | 43 | $CH_3NH_2$ | 1-methyl |
| 110 | 71 | $CH_3NH_2$ | 10-ethyl-1-methyl-7-nitro |
| 111 | 72 | $C_3H_7NH_2$ | 5-ethyl-9-isopropyl-1-propyl |
| 112 | 73 | $NH_3$ | 5-(4-butanol)-7-ethoxy-8-iodo |
| 113 | 74 | $NH_3$ | 8-chloro-9-nitro-5-propyl |
| 114 | 75 | $NH_3$ | 9-bromo-10-nitro-5-(2-propoxyethyl) |
| 115 | 76 | $C_5H_{11}NH_2$ | 10-bromo-8-fluoro-1-pentyl |
| 116 | 77 | $NH_3$ | 8-ethoxy-10-iodo-5-[(4-ethyl-4-methoxy)-butyl] |
| 117 | 78 | $NH_3$ | 8-ethyl-9-(1-methylpropyl)-5-(3-propanol) |

EXAMPLE 118

9-Butyl-1,4-dihydro-4-oxo-5H-[1]benzothiopyrano[4,3-b]pyridine-2-carboxylic acid Methyl Ester (1; $R^1$,$R^3$,$R^4$ and $R^5$ = H, $R^2$ = $C_4H_9$, $R^{15}$ = $CH_3$, X = S and Y = NH)

A solution of 9 -1,4-dihydro-4-oxo-5H-[1]benzothiopyrano[4,3-b]pyridine-2-carboxylic acid (1.82 g, described in Example 84) in 350 ml of anhydrous methanol saturated with hydrogen chloride is heated at reflux for 17 hours. The slovent is removed by evaporation. Water is added to the residue and the aqueous mixture is extracted with chloroform. The organic extract is dried over magnesium sulfate and evaporated. The residue is subjected to chromatography on silica gel using benzene-ethyl acetate (4:1) as eluant. The eluate is evaporated and the residue is crystallized from ether to give the title compound, m.p. 144°-146° C.

In the same manner but replacing 9-butyl-1,4-dihydro-4-oxo-5H-[1]benzothiopyrano[4,3-b]pyridine-2carboxylic acid with an equivalent amount of 9 -(1-methylpropyl)-1,4-dihydro-4-oxo-5H-[1]benzothiopyrano[4,3-b]pyridine-2-carboxylic acid (described in Example 99) and replacing methanol with ethanol, 9-(1-methylpropyl)-1,4-dihydro-4-oxo-5H-[1]benzothiopyrano[4,3-b]pyridine-2-carboxylic acid ethyl ester (1; $R^1$, $R^3$, $R^4$ and $R^5$ = H,$R^2$ = $CH(CH_3)C_2H_5$, $R^{15}$ = $C_2H_5$, X = S and Y =NH), nmr (DMSO-$d_6$) δ 0.83 (t, J=7Hz, 3H), 1.2 – 1.52 (M, 9H), 4.09 (S, 2H), 4.41 (q, J=6.5Hz, 2H), 7.31 (m, 3H), 7.63 (S, 1H) and 8.25 (S, 1H), is obtained.

In the same manner other γ-pyridone esters of formula 1 in which $R^{15}$ is lower alkyl and Y is $NR^{16}$ are prepared, for example, replacing 9-butyl-1,4-dihydro-4-oxo-5H-[1]benzothiopyrano[4,3-b]pyridine-2-carboxylic acid with an equivalent amount of the title compound of Example 81, 82, 85, 100, 104, 110 or 113 and using an appropriate lower alkanol as solvent, the following γ-pyridone esters of formula 1 are obtained respectively, 5-methyl-1,4-dihydro-4-oxo-5H-[1]benzothiopyrano[4,3-b]pyridine-2-carboxylic acid methyl ester, 9-chloro-1,4-dihydro-4-oxo-5H[1]benzothiopyrano[4,3-b]pyridine-2-carboxylic acid propyl ester, 10-chloro-7-methyl-1,4-dihydro-4-oxo-5H-[1]benzothiopyrano[4,3-b]pyridine-2-carboxylic acid butyl ester, 1-ethyl-1,4-dihydro-4-oxo-5H-[1]benzothiopyrano[4,3-]pyridine-6-oxide-2-carboxylic acid methyl ester, 1,4-dihydro-4-oxo-5H-[1]benzothiopyrano[4,3-b]pyridine-6,6-dioxide-2-carboxylic acid ethyl ester, 10-ethyl-1-methyl-7-nitro-1,4-dihydro-4-oxo-5H[1]benzopyrano[4,3-pyridine-2-carboxylic acid pentyl ester and 8-chloro-9-nitro-5-propyl-1,4-dihydro-4-oxo-5H-[1]benzopyrano[4,3-b]pyridine-2-carboxylic acid ethyl ester.

We claim:
1. A compound of formula 1

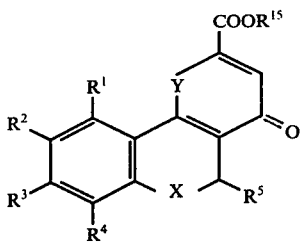

I in which $R^1$, $R^2$, $R^3$ and $R^4$ are the same or different selected from the group consisting of hydrogen halogen and lower alkyl; $R^5$ is hydrogen or lower alkyl; $R^{15}$ is hydrogen or lower alkyl; X is O, S, SO or $SO_2$; and Y is O or a pharmaceutically acceptable salt thereof.

2. 4-Oxo-4H,5H-[1]benzopyrano[4,3-b]pyran-2-carboxylic acid, as claimed in claim 1.

3. 5-Methyl-4-oxo-4H,5H-[1]benzothiopyrano[4,3-b]pyran-2-carboxylic acid, as claimed in claim 1.

4. 4-Oxo-4H,5H[1]benzothiopyrano4,3-b]pyran-2-carboxylic acid, as claimed in claim 1.

5. 9-Chloro-4-oxo-4H,5H-[1]benzothiopyrano[4,3-]pyran-2-carboxylic acid, as claimed in claim 1.

6. 9-Methyl-4-oxo-4H,5H-[1]benzothiopyrano[4,3-b]pyran-2-carboxylic acid, as claimed in claim 1.

7. 9-Butyl-4-oxo-4H,5H-[1]benzothiopyrano[4,3-b]-2-caraoxylic acid, as claimed in claim 1.

8. 10-Chloro-7-methyl-4-oxo-4H,5H-[1]benzothiopyrano[4,3-b]pyran-2-carboxylic acid, as claimed in claim 1.

9. 9-(1-Methylpropyl)-4-oxo-4H,5H-[1]benzothiopyrano[4,3-b]pyran-2-carboxylic acid, as claimed in claim 1.

10. 4-Oxo-4H,5H-[1]benzothiopyrano[4,3-b]pyran-2-carboxylic acid-6,6-dioxide, as claimed in claim 1.

11. 4-Oxo-4H,5H-[1]benzopyrano[4,3-b]pyran-2carboxylic acid methyl ester, as claimed in claim 1.

12. 5-Methyl-4-oxo-4-4H,5H-[1]benzothiopyrano[4,3-b]pyran-2carboxylic acid methyl ester, as claimed in claimed in claim 1.

13. 9-Chloro-4H,5H-[1]benzothiopyrano[4,3-b]pyran-2-carboxylic acid methyl ester, as claimed in claim 1.

14. 9-Methyl-4H,5H-[1]benzothiopyrano[4,3-b]pyran-2-carboxylic acid methyl ester, as claimed in claim 1.

15. 9-Butyl-4H,5H-[1]benzothiopyrano[4,3-b]pyran-2-carboxylic acid methyl ester, as claimed in claim 1.

16. 10-Chloro-7-methyl-4H,5H-[1]benzothiopyrano[4,3-b]-pyran-2-carboxylic acid methyl ester, as claimed in claim 1.

17. 4-Oxo-4H,5H-[1]benzothiopyrano[4,3-b]pyran-6,6-dioxide-2-carboxylic acid methyl ester, as claimed in claim 1.

18. A method for treating allergic conditions in a mammal which comprises administering to said mammal an effective amount of a compound of claim 1 or a pharmaceutically acceptable salt thereof.

19. An antiallergic pharmaceutical composition comprising an effective amount of a compound or a pharmaceutically acceptable salt thereof as defined in claim 1, and a pharmaceutically acceptable carrier.

20. A compound having the nucleus

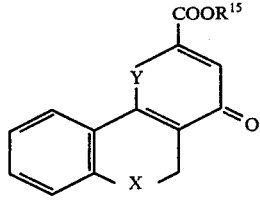

in which X is O,S,SO and $SO_2$; and Y is O.

* * * * *